US012642869B2

(12) United States Patent
Kügler

(10) Patent No.: US 12,642,869 B2
(45) Date of Patent: Jun. 2, 2026

(54) REGULATABLE ADENO-ASSOCIATED VIRUS (AAV) VECTOR

(71) Applicant: GEORG-AUGUST-UNIVERSITÄT GÖTTINGEN STIFTUNG ÖFFENTLICHEN RECHTS, UNIVERSITÄTSMEDIZIN, Göttingen (DE)

(72) Inventor: Sebastian Kügler, Göttingen (DE)

(73) Assignee: GEORG-AUGUST-UNIVERSITÄT GÖTTINGEN STIFTUNG ÖFFENTLICHEN RECHTS, UNIVERSITÄTSMEDIZIN, Göttingen (DE)

( * ) Notice: Subject to any disclaimer, the term of this patent is extended or adjusted under 35 U.S.C. 154(b) by 1075 days.

(21) Appl. No.: 17/559,538

(22) Filed: Dec. 22, 2021

(65) Prior Publication Data

US 2022/0193263 A1 Jun. 23, 2022

Related U.S. Application Data

(62) Division of application No. 15/494,125, filed on Apr. 21, 2017, now abandoned.

(30) Foreign Application Priority Data

Apr. 22, 2016 (EP) ..................................... 16166637

(51) Int. Cl.
| | |
|---|---|
| C12N 15/864 | (2006.01) |
| A61K 48/00 | (2006.01) |
| C07K 14/475 | (2006.01) |
| C12N 15/11 | (2006.01) |
| C12N 15/64 | (2006.01) |
| C12N 15/86 | (2006.01) |

(52) U.S. Cl.
CPC .......... *A61K 48/0008* (2013.01); *A61K 48/00* (2013.01); *A61K 48/005* (2013.01); *A61K 48/0058* (2013.01); *C07K 14/475* (2013.01); *C12N 15/86* (2013.01); *C12N 2750/14143* (2013.01); *C12N 2830/002* (2013.01); *C12N 2830/008* (2013.01); *C12N 2830/34* (2013.01); *C12N 2830/40* (2013.01); *C12N 2830/42* (2013.01); *C12N 2830/50* (2013.01); *C12N 2830/702* (2013.01); *C12N 2830/85* (2013.01); *C12N 2840/007* (2013.01); *C12N 2840/60* (2013.01)

(58) Field of Classification Search
None
See application file for complete search history.

(56) References Cited

U.S. PATENT DOCUMENTS

2006/0292609 A1 12/2006 Bauzon et al.

FOREIGN PATENT DOCUMENTS

| WO | 2002/024899 A2 | 3/2002 |
|---|---|---|
| WO | 2002/097099 A1 | 12/2002 |
| WO | 2004/061104 A2 | 7/2004 |
| WO | 2005/087926 A2 | 9/2005 |
| WO | 2007/134906 A1 | 1/2007 |
| WO | 2009/045370 A2 | 4/2009 |
| WO | 2012/122025 A2 | 9/2012 |

OTHER PUBLICATIONS

Aker, et al. "Extended core sequences from the cHS4 insulator are necessary for protecting retroviral vectors from silencing position effects." Human gene therapy 18, No. 4 (2007): 333-343.
Bartus, et al. "Safety/feasibility of targeting the substantia nigra with AAV2-neurturin in Parkinson patients." Neurology 80, No. 18 (2013): 1698-1701.
Burcin, et al. "Adenovirus-mediated regulable target gene expression in vivo." Proceedings of the National Academy of Sciences 96, No. 2 (1999): 355-360.
Chtarto, et al.,. Tetracycline-inducible transgene expression mediated by a single AAV vector. Gene therapy, 10(1), Jan. 1, 2003, pp. 84-94.
Chtarto, et al. "A next step in adeno-associated virus-mediated gene therapy for neurological diseases: Regulation and targeting." British journal of clinical pharmacology 76, No. 2 (2013): 217-232.
Cheng et al. Therapeutic efficacy of regulable GDNF expression for Huntington's and Parkinson's disease by a high-induction, background-free "GeneSwitch" vector. Experimental neurology. Nov. 1, 2018;309:79-90.
Chung, et al. "A 5' element of the chicken β-globin domain serves as an insulator in human erythroid cells and protects against position effect in *Drosophila*." Cell 74, No. 3 (1993): 505-514.
Dogbevia, et al. "Flexible, AAV-equipped genetic modules for inducible control of gene expression in mammalian brain." Molecular Therapy-Nucleic Acids 5 (2016): e309, 1-8.
Drinkut, et al. "Efficient gene therapy for Parkinson's disease using astrocytes as hosts for localized neurotrophic factor delivery." Molecular therapy 20, No. 3 (2012): 534-543.
Gromak, et al. "Pause sites promote transcriptional termination of mammalian RNA polymerase II." Molecular and cellular biology 26, No. 10 (2006): 3986-3996.
Jiang, et al. "Tight regulation from a single tet-off rAAV vector as demonstrated by flow cytometry and quantitative, real-time PCR." Gene therapy 11, No. 13 (2004): 1057-1067.
Kordower, et al. "Trophic factor gene therapy for Parkinson's disease." Movement Disorders 28, No. 1 (2013): 96-109.
Lesk et al. Prediction of protein function from protein sequence and structure. Quarterly reviews of biophysics. Aug. 2003;36(3):pp. 27-28.

(Continued)

*Primary Examiner* — Maria Marvich
(74) *Attorney, Agent, or Firm* — Kilpatrick Townsend & Stockton LLP

(57) ABSTRACT

The present invention relates to regulatable adeno-associated virus (AAV) vectors as well as to their use in gene therapy. It further relates to corresponding nucleic acid molecules, host cells, non-human transgenic animals, pharmaceutical compositions and kits.

19 Claims, 2 Drawing Sheets

Specification includes a Sequence Listing.

(56)                    References Cited

OTHER PUBLICATIONS

Liu, et al. "Protection against aminoglycoside-induced ototoxicity by regulated AAV vector-mediated GDNF gene transfer into the cochlea." Molecular Therapy 16, No. 3 (Jan. 8, 2008): 474-480.

Liu et al. Enhancement of cell-specific transgene expression from a Tet-Off regulatory system using a transcriptional amplification strategy in the rat brain. The Journal of Gene Medicine: A cross-disciplinary journal for research on the science of gene transfer and its clinical applications. May 2008;10(5):583-92.

Maclaren et al. "Retinal gene therapy in patients with choroideremia: initial findings from a phase 1/2 clinical trial." The Lancet 383, No. 9923 (2014): 1129-1137.

Maddalena, et al. "Adeno-associated virus-mediated, mifepristone-regulated transgene expression in the brain." Molecular Therapy-Nucleic Acids 2 (Jul. 1, 2013): e106.

Manfredsson, et al. "Tight Long-term dynamic doxycycline responsive nigrostriatal GDNF using a single rAAV vector." Molecular Therapy 17, No. 11 (Nov. 25, 2009): 1857-1867.

Naidoo, et al. "Gene regulation systems for gene therapy applications in the central nervous system." Neurology research international (Jan. 1, 2012) 267 (5202), 10 pages.

Oligino, et al. "Drug inducible transgene expression in brain using a herpes simplex virus vector." Gene therapy 5, No. 4 (1998): 491-496.

Palfi, et al. "Long-term safety and tolerability of ProSavin, a lentiviral vector-based gene therapy for Parkinson's disease: a dose escalation, open-label, phase 1/2 trial." The Lancet 383, No. 9923 (2014): 1138-1146.

Papadakis ED, Nicklin SA, Baker AH, White SJ. Promoters and control elements: designing expression cassettes for gene therapy. Current gene therapy. Mar. 1, 2004;4(1):89-113.

Tereshchenko, et al. "Pharmacologically controlled, discontinuous GDNF gene therapy restores motor function in a rat model of Parkinson's disease." Neurobiology of disease 65 (2014): 35-42.

Tian, et al. "Independent and high-level dual-gene expression in adult stem-progenitor cells from a single lentiviral vector." Gene therapy 16, No. 7 (2009): 874-884.

Vilaboa, et al. "Gene switches for deliberate regulation of transgene expression: recent advances in system development and uses." J Genet Syndr Gene Ther 2, No. 107 (2011): 1-23.

Wang, et al. "A regulatory system for use in gene transfer." Proceedings of the National Academy of Sciences 91, No. 17 (1994): 8180-8184.

Wang, et al. "Positive and negative regulation of gene expression in eukaryotic cells with an inducible transcriptional regulator." Gene therapy 4, No. 5 (1997): 432-441.

REGULATABLE ADENO-ASSOCIATED VIRUS (AAV) VECTOR

CROSS-REFERENCE TO RELATED APPLICATION

This patent application is a division of U.S. application Ser. No. 15/494,125, filed Apr. 21, 2017, which claims the benefit of priority from European Patent Application No. 16 166 637.5, filed on Apr. 22, 2016, the contents of each of which are hereby incorporated by reference in the entirety.

REFERENCE TO A SEQUENCE LISTING

A sequence listing containing SEQ ID NOs:1-2 is submitted herewith and is specifically incorporated by reference.

FIELD OF THE INVENTION

The present invention relates to regulatable adeno-associated virus (AAV) vectors as well as to their use in gene therapy. It further relates to corresponding nucleic acid molecules, host cells, non-human transgenic animals, pharmaceutical compositions and kits.

BACKGROUND OF THE INVENTION

Gene therapy in its current configuration is an irreversible process. Typically, a potentially therapeutic transgene is inserted into target cells/tissues by means of gene transfer with a viral vector. From this time on, the transgene is expressed without external control over its expression level and without the option to shut off transgene expression in case of unforeseen side effects or sufficient therapeutic success.

Attempts to overcome this limitation have generated several regulatable gene transfer systems, one of which is the gene switch (GS), whose principles are described in FIG. 1. A constitutive promoter (which may be cell-type specific or ubiquitously active) expresses the GS fusion protein, which consists of a GAL4 DNA binding domain, a truncated progesterone receptor ligand binding domain as drug binding domain, and the p65 transactivation domain from NF-kappaB. Upon binding of the GS fusion protein to the small molecule drug mifepristone (Mfp, a synthetic steroid), it dimerizes and binds to a polynucleotide sequence consisting of several GAL4 DNA binding sites. Consequently, the p65 moiety of the GS fusion protein recruits the basic cellular transcription machinery, allowing expression of the therapeutic factor from a minimal promoter. Withdrawal of Mfp disables binding of the GS fusion protein to its DNA target sequence, and thus ceases transgene expression.

The GS system was described for plasmids, transgenic cells, adenoviral and herpes simplex gene transfer vectors and for transgenic animals during the 1990's (Wang Y. et al., Proc. Natl. Acad. Sci. USA. 1994, 91:8180-8184; Wang Y. et al., Gene Ther. 1997, 4:432-441; Burcin M. M. et al., Proc. Natl. Acad. Sci. USA. 1999, 96:355-360; Oligino T. et al., Gene Ther. 1998, 5:491-496). As adeno-associated viral vectors (AAVs) are especially well-suited gene therapy tools due to their proven safety record in human clinical trials (Bartus R. T. et al., Neurology. 2013, 80:1698-1701; Chtarto A. et al., Br J Clin Pharmacol. 2013, 76:217-232), the inventor has adopted the GS system to AAV vectors. Using the brain as target tissue and Parkinson's disease as a target disease, the inventor demonstrated successful therapeutic treatment of motor symptoms in a rat model of Parkinson's disease (Tereshchenko J. et al., Neurobiol Dis. 2014, 65:35-42; Maddalena A. et al., Mol Ther Nucleic Acids. 2013, 2:e106). In this approach, the inventor was able to show that short-term induced expression of the neurotrophic factor GDNF (glial cell line-derived neurotrophic factor, Kordower J. H. et al., Mov Disord. 2013, 28:96-109) resulted in long-term recovery from motor impairments in this model.

A functional GS system usually requires gene transfer of two expression cassettes into target cells: one cassette expressing the GS fusion protein and a second cassette expressing the therapeutic factor from the regulated minimal promoter. Accordingly, the above-mentioned studies were conducted with a two-vector system, in which the GS expression cassette was contained in one virus, while the regulated GDNF expression cassette was contained in a second virus. This configuration was necessary to prevent leaky expression of GDNF in the non-Mfp-induced state (Maddalena A. et al., Mol Ther Nucleic Acids. 2013, 2:e106). While such a two-vector system offers flexibility in terms of adjusting the ratio of GS expression cassette versus the GDNF expression cassette, it appears unlikely that such a double vector formulation could be approved by authorities for human gene therapy.

A one-vector system described in Maddalena A. et al. (Mol Ther Nucleic Acids. 2013, 2:e106) exhibits leaky expression of GDNF in the non-Mfp-induced state. Other regulated vector systems, e.g., as described in Liu Y. et al. (Molecular Therapy. 2008, 16(3):474-480) and Naidoo J. et al. (Neurology Research Int. 2012, 267, No. 5202), are based on the use of active transcriptional silencers, such as the Tet repressor, and/or are based on viruses, which will hamper or prevent the clinical use of these systems.

Thus, there is a need in the art for a regulated AAV vector-based expression system with at least the following features:

- all elements of the system (e.g., GS system) for regulated expression of a therapeutic molecule (e.g., a neurotrophic factor, such as GDNF) should be contained in one vector genome;
- after injection of this vector into the patient (e.g., into a specific tissue/organ, such as the brain), it should not express the therapeutic molecule in the absence of the activator molecule (e.g., Mfp);
- after application of the activator molecule, levels of the therapeutic molecule should increase substantially to levels of therapeutic value; and
- after withdrawal of the activator molecule levels of the therapeutic molecule should decline to background levels again.

SUMMARY OF THE INVENTION

In one aspect, the present invention relates to an adeno-associated virus (AAV) vector comprising

- (i) a first expression cassette directing the expression of a regulator protein under the control of a first promoter, wherein the regulator protein is activated in the presence of an activator molecule, and
- (ii) a second expression cassette directing the expression of a molecule of interest, wherein the second expression cassette comprises a promoter region, and the expression of the molecule of interest is induced by binding of the activated regulator protein to the promoter region, wherein the first expression cassette and the second expression cassette are arranged in a tail-to-head configuration.

In one embodiment, the first promoter has one or more of the following features:

(i) it is a constitutive promoter;

(ii) it is selected from the group consisting of cell-specific promoters, tissue-specific promoters and organ-specific promoters;

(iii) it is selected from the group consisting of human synapsin 1 gene (hSYN1) promoter, tubulin alpha 1 (Tal) promoter, glial fibrillary acidic protein (GFAP) promoter, cytomegalovirus (CMV) promoter, human beta-actin-CMV hybrid promoter and functional fragments or variants of any of the foregoing.

In one embodiment, the regulator protein is a gene switch fusion protein comprising a GAL4 DNA binding domain, a truncated progesterone receptor ligand binding domain and a p65 transactivation domain from NF-kappaB.

In one embodiment, the activator molecule is mifepristone (Mfp).

In one embodiment, the first expression cassette comprises, in 5' to 3' direction, the first promoter, a coding sequence for the regulator protein and a first polyadenylation signal sequence, wherein, optionally, the first expression cassette further comprises a synthetic intron arranged between the coding sequence for the regulator protein and the first polyadenylation signal sequence.

In one embodiment, the promoter region comprises one or more binding sites for the activated regulator protein, a second promoter and, optionally, a synthetic intron.

In one embodiment, the one or more binding sites for the activated regulator protein are GAL4 binding sites.

In one embodiment, the second promoter is a minimal promoter which is induced by the binding of the activated regulator protein to the one or more binding sites for the activated regulator protein.

In one embodiment, the second promoter is a minimal promoter comprising a TATA sequence and/or an mRNA initiation sequence.

In one embodiment, the molecule of interest is a therapeutically active peptide or protein or a therapeutically active oligo- or polynucleotide.

In one embodiment, the molecule of interest is a neurotrophic factor.

In one embodiment, the second expression cassette comprises, in 5' to 3' direction, the promoter region, a coding sequence for the molecule of interest and a second polyadenylation signal sequence.

In one embodiment, the first expression cassette and the second expression cassette are separated by a nucleotide sequence comprising an insulator element.

In one embodiment, the insulator element is a transcription blocker comprising a transcription pause site and a polyadenylation signal sequence.

In one embodiment, the AAV vector comprises the nucleotide sequence represented by SEQ ID NO:

1 or a functional variant thereof, wherein the functional variant has a nucleotide sequence which is at least 80% or at least 85% or at least 90% or at least 95% identical to SEQ ID NO: 1.

In one embodiment, in the absence of the activator molecule, the molecule of interest is not expressed in a host or is expressed in a host at a level which is at most 10-fold or at most 5-fold or at most 4-fold or at most 3-fold or at most 2-fold increased as compared to the normal expression level of the molecule of interest in the host, wherein the host is a cell, tissue or organ.

In another aspect, the present invention relates to an adeno-associated virus (AAV) vector construct comprising (i) a first expression cassette directing the expression of a regulator protein under the control of a first promoter, wherein the regulator protein is activated in the presence of an activator molecule, and (ii) a second expression cassette comprising a multiple cloning site allowing the insertion of a coding sequence for a molecule of interest, wherein the second expression cassette comprises a promoter region, and the expression of the molecule of interest is induced by binding of the activated regulator protein to the promoter region, wherein the first expression cassette and the second expression cassette are arranged in a tail-to-head configuration.

In one embodiment, the AAV vector construct comprises the nucleotide sequence represented by SEQ ID NO: 2 or a functional variant thereof, wherein the functional variant has a nucleotide sequence which is at least 80% or at least 85% or at least 90% or at least 95% identical to SEQ ID NO: 2.

In another aspect, the present invention relates to the AAV vector as defined above, wherein the molecule of interest is a therapeutically active peptide or protein or a therapeutically active oligo- or polynucleotide, for use as a medicament.

In another aspect, the present invention relates to the AAV vector as defined above, wherein the molecule of interest is a neurotrophic factor, for use in treating, ameliorating or preventing a disease or disorder selected from the group consisting of Parkinson's disease, Huntington's disease, spinal cord lesion and an amyloid-related disorder, wherein, preferably, the amyloid-related disorder is selected from the group consisting of Alzheimer's disease (e.g., sporadic Alzheimer's disease or familial Alzheimer's disease), cerebral amyloid angiopathy, dementia, motor neuropathy, Down's syndrome, Creutzfeld Jacob disease, transmissible spongiform encephalopathies, hereditary cerebral hemorrhage with amyloidosis Dutch type, HIV-related dementia, fronto-temporal dementia, Lewy body disease, mixed dementias, head trauma, familial Danish Dementia, familial British Dementia, inclusion body myositis (IBM), neuronal disorder related to aging, and chronic pain.

In another aspect, the present invention relates to the use of the AAV vector as defined above for the preparation of a medicament for treating, ameliorating or preventing a disease or disorder in a subject, wherein the molecule of interest is a therapeutically active peptide or protein or therapeutically active oligo- or polynucleotide.

In another aspect, the present invention relates to a method for treating, ameliorating or preventing a disease or disorder in a subject, comprising (a) introducing into the subject the AAV vector as defined above; and (b) administering to the subject the activator molecule to induce expression of the molecule of interest, wherein the molecule of interest is a therapeutically active peptide or protein or therapeutically active oligo- or polynucleotide.

In some embodiments of said use or said method, the molecule of interest is a neurotrophic factor and the disease or disorder is selected from the group consisting of Parkinson's disease, Huntington's disease, spinal cord lesion and an amyloid-related disorder, wherein, preferably, the amyloid-related disorder is selected from the group consisting of Alzheimer's disease (e.g., sporadic Alzheimer's disease or familial Alzheimer's disease), cerebral amyloid angiopathy, dementia, motor neuropathy, Down's syndrome, Creutzfeld Jacob disease, transmissible spongiform encephalopathies, hereditary cerebral hemorrhage with amyloidosis Dutch type, HIV-related dementia, fronto-temporal dementia, Lewy body disease, mixed dementias, head trauma, familial Danish Dementia, familial British Dementia, inclusion body myositis (IBM), neuronal disorder related to aging, and chronic pain.

In another aspect, the present invention relates to a host cell comprising the AAV vector as defined above.

In another aspect, the present invention relates to a non-human transgenic animal comprising the AAV vector as defined above.

In another aspect, the present invention relates to a pharmaceutical composition comprising the AAV vector as defined above or the host cell as defined above.

In yet another aspect, the present invention relates to a kit comprising the AAV vector as defined above or the AAV vector construct as defined above or the host cell as defined above or the pharmaceutical composition as defined above.

DETAILED DESCRIPTION OF THE INVENTION

Figure 1:
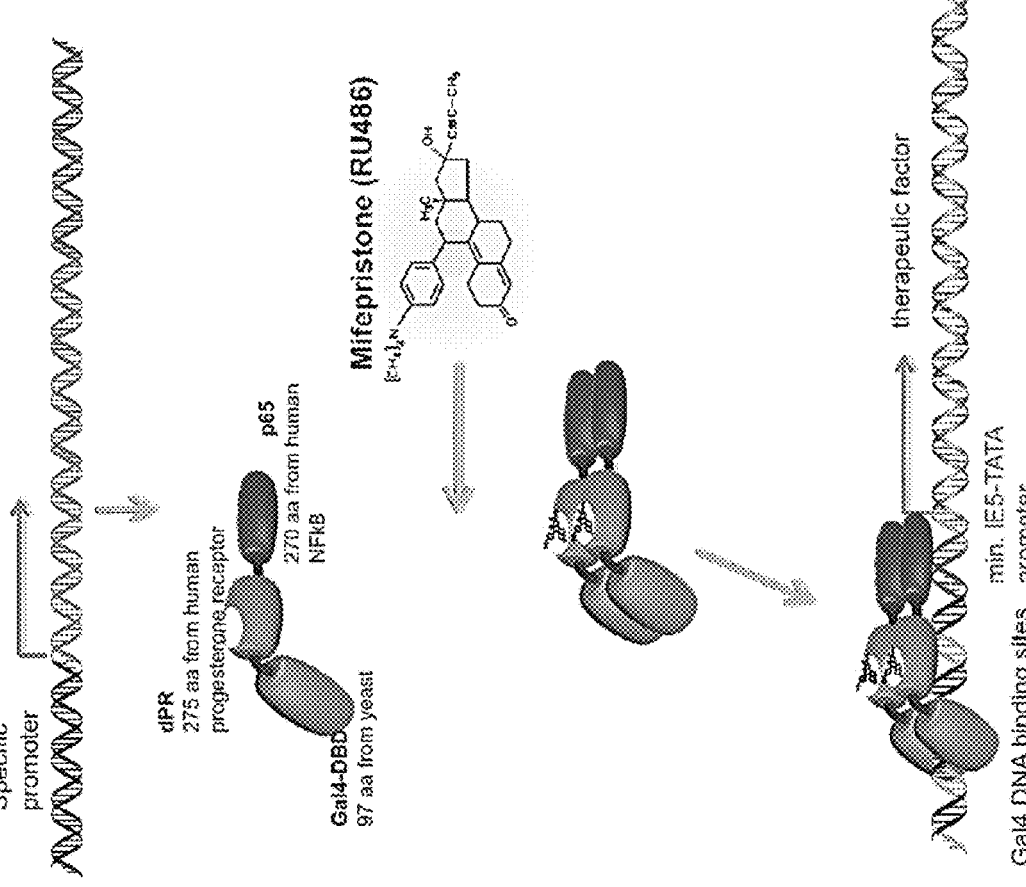
FIG. 1 shows the components of the gene switch (GS) system.

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention, which will be limited only by the appended claims. Unless defined otherwise, all technical and scientific terms used herein have the same meanings as commonly understood by one of ordinary skill in the art. Preferably, the terms used herein are defined as described in "A multilingual glossary of biotechnological terms (IUPAC Recommendations)", H. G. W. Leuenberger, B. Nagel, and H. Kölbl, Eds., Helvetica Chimica Acta, CH-4010 Basel, Switzerland, (1995). The practice of the present invention will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 3rd Edition, J. Sambrook et al. eds., Cold Spring Harbor Laboratory Press, Cold Spring Harbor 2000).

In the following, certain elements of the present invention will be described. These elements may be listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments, which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The present invention provides an adeno-associated virus (AAV) vector comprising (i) a first expression cassette directing the expression of a regulator protein under the control of a first promoter, wherein the regulator protein is activated in the presence of an activator molecule, and (ii) a second expression cassette directing the expression of a molecule of interest, wherein the second expression cassette comprises a promoter region, and the expression of the molecule of interest is induced by binding of the activated regulator protein to the promoter region, wherein the first expression cassette and the second expression cassette are arranged in a tail-to-head configuration.

As used herein, the term "adeno-associated virus (AAV) vector" means an AAV viral particle containing an AAV vector genome (which, in turn, comprises the first and second expression cassettes referred to herein). It is meant to include AAV vectors of all serotypes, preferably AAV-1 through AAV-9, more preferably AAV-1, AAV-2, AAV-4, AAV-5, AAV-6, AAV-7, AAV-8, AAV-9, and combinations thereof. AAV vectors resulting from the combination of different serotypes may be referred to as hybrid AAV vectors. In one embodiment, the AAV vector is selected from the group consisting of AAV-1, AAV-2, AAV-4, AAV-5 and AAV-6, and combinations thereof. In one embodiment, the AAV vector is an AAV-5 vector. In one embodiment, the AAV vector is an AAV-5 vector comprising AAV-2 inverted terminal repeats (ITRs). Also included in the present invention are AAV vectors comprising variants of the naturally occurring viral proteins, e.g., one or more capsid proteins. In one embodiment, the one or more variant capsid proteins comprise the substitution of one or more amino acid residues, thereby modifying, preferably improving, the vector transduction properties. Suitable variants of AAV viral proteins are known to the skilled person.

The term "expression cassette", as used herein, refers to a nucleotide sequence which directs the cell's machinery (or any other transcription active system, such as an in vitro transcription/translation system) to express/make a particular functional product. Generally, an expression cassette comprises a promoter sequence, an open reading frame (also referred to as coding region) coding, e.g., for a peptide or protein, and a 3' untranslated region (3' UTR), which preferably contains a polyadenylation signal sequence. An expression cassette according to the present invention may further comprise a 5' untranslated region (5' UTR), which is located 3' of the promoter (region) and 5' of the coding region.

The term "tail-to-head configuration", as used herein, means that, in the AAV vector, (i) the 3' end of the first expression cassette is adjacent to the 5' end of the second expression cassette or (ii) the 3' end of the second expression cassette is adjacent to the 5' end of the first expression cassette. In other words, the first expression cassette and the second expression cassette are oriented in the same transcriptional direction. In a preferred embodiment, the 3' end of the first expression cassette is adjacent to the 5' end of the second expression cassette.

In accordance with the present invention, "adjacent" can be "directly adjacent" or "indirectly adjacent". The term "indirectly adjacent", as used herein, refers to the situation where the first expression cassette and the second expression cassette are separated by a nucleotide sequence. In one embodiment, the nucleotide sequence consists of less than 1500 nucleotides, less than 1000 nucleotides, less than 500 nucleotides, less than 250 nucleotides, less than 200 nucleotides, or less than 150 nucleotides. In one embodiment, the nucleotide sequence comprises, essentially consists of or consists of an insulator element.

The term "insulator element", as used herein, refers to a nucleotide sequence, preferably a synthetic nucleotide sequence, reducing or preventing expression of the molecule of interest in the absence of the activator molecule. Such nucleotide sequences are known to a person skilled in the art. In one embodiment, the insulator element is a transcription blocker (TB) comprising, essentially consisting of or consisting of a transcription pause site and a polyadenylation signal sequence (also referred to herein as a polyadenylation site).

In one embodiment, the first promoter is a constitutive promoter. The term "constitutive promoter", as used herein, refers to an unregulated promoter that allows for continual transcription of its associated gene.

In one embodiment, the first promoter is selected from the group consisting of human synapsin 1 gene (hSYN1) promoter, tubulin alpha 1 (Tal) promoter, glial fibrillary acidic protein (GFAP) promoter, cytomegalovirus (CMV) promoter, human beta-actin-CMV hybrid promoter and functional fragments or variants of any of the foregoing.

In one embodiment, the first promoter allows for ubiquitous expression of the regulator protein and is preferably selected from the group consisting of cytomegalovirus (CMV) promoter, human beta-actin-CMV hybrid promoter and functional fragments or variants of any of the foregoing.

In one embodiment, the first promoter is selected from the group consisting of cell-specific promoters, tissue-specific promoters and organ-specific promoters. In one embodiment, the promoter is a neuron-specific promoter or an astrocyte-specific promoter. In one embodiment, the neuron-specific promoter is selected from the group consisting of human synapsin 1 gene (hSYN1) promoter, tubulin alpha 1 (Tal) promoter and functional fragments or variants of any of the foregoing. In one embodiment, the neuron-specific promoter is human synapsin 1 gene (hSYN1) promoter or a functional fragment or variant thereof. In one embodiment, the astrocyte-specific promoter is glial fibrillary acidic protein (GFAP) promoter or a functional fragment or variant thereof.

The term "regulator protein", as used herein, refers to a protein (e.g., a fusion protein), which, upon interaction with an activator molecule (in particular, upon binding of the activator molecule to the regulator protein), undergoes a conformational change to an activated state and binds to the promoter region of the second expression cassette, thereby inducing the expression of the molecule of interest. According to the present invention, the regulator protein does not bind to the promoter region of the second expression cassette in its inactive state. In one embodiment, the regulator protein is a fusion protein comprising a (truncated) progesterone receptor ligand binding domain. In one embodiment, the fusion protein is a gene switch fusion protein. Suitable gene switch fusion proteins that can be used in accordance with the present invention are described, for example, in WO 2002/24899 A2, WO 2009/045370 A2, Wang Y. et al., Proc. Natl. Acad. Sci. USA. 1994, 91:8180-8184, and Wang Y. et al., Gene Ther. 1997, 4:432-441. In one embodiment, the regulator protein is a gene switch fusion protein comprising, essentially consisting of or consisting of a GAL4 DNA binding domain (e.g., amino acids 1 to 93 of S. cerevisiae GAL4), a truncated progesterone receptor ligand binding domain (e.g., amino acids 640 to 914 of human progesterone receptor) and a p65 transactivation domain from NF-kappaB (e.g., amino acids 283 to 551 of the human p65 subunit of NF-kappaB).

The term "activator molecule", as used herein, refers to a molecule (e.g., a small molecule compound) that activates the regulator protein in vivo and is, preferably, pharmaceutically acceptable. Preferably, the activator molecule is a ligand of the regulator protein, wherein activation of the regulator protein may, for example, comprise the dimerization of the regulator protein. Suitable activator molecules that can be used in accordance with the present invention are described, for example, in WO 2002/24899 A2, WO 2009/045370 A2, Wang Y. et al., Proc. Natl. Acad. Sci. USA. 1994, 91:8180-8184, and Wang Y. et al., Gene Ther. 1997, 4:432-441. In one embodiment, the activator molecule is an anti-progestin. In one embodiment, the activator molecule is mifepristone (Mfp; RU486).

A commercially available gene switch system that can be used in accordance with the present invention is the Gene-Switch™ System (ThermoFisher Scientific).

The AAV vector of the present invention may comprise one or more introns. The term "intron" as used herein refers to a sequence encoded in a DNA sequence that is transcribed into an RNA molecule by RNA polymerase but is removed by splicing to form the mature messenger RNA. A "synthetic intron" refers to a sequence that is not initially replicated from a naturally occurring intron sequence and generally will not have a naturally occurring sequence, but will be removed from an RNA transcript during normal post-transcriptional processing. Preferably, the synthetic intron includes consensus sequences for the 5' splice site, 3' splice site, and, optionally, the branch point. Such synthetic intron, when introduced into the AAV vector of the present invention, may direct the splicing of RNA transcripts in a highly efficient and accurate manner, thereby minimizing cryptic splicing and maximizing production of the desired gene product, e.g., the regulator protein and/or the molecule of interest. In one embodiment, the synthetic intron is an IVS8 synthetic intron.

In one embodiment, the AAV vector of the present invention does not comprise a(n) (active) transcriptional silencer, such as a Tet repressor.

In one embodiment, the first expression cassette comprises or essentially consists of, in 5' to 3' direction, the first promoter, a coding sequence for the regulator protein and a first polyadenylation signal sequence. Optionally, the first expression cassette further comprises a synthetic intron arranged between the coding sequence for the regulator protein and the first polyadenylation signal sequence and/or a synthetic intron located in the 5' UTR, if present.

In one embodiment, the promoter region in the second expression cassette comprises, essentially consists of or consists of one or more binding sites for the activated regulator protein, a second promoter and, optionally, a synthetic intron.

In one embodiment, the one or more binding sites for the activated regulator protein are GAL4 binding sites, also referred to herein as GAL4 upstream activating sequences (UAS). In one embodiment, the promoter region comprises six GAL4 binding sites.

In one embodiment, the second promoter is a minimal promoter which is induced by the binding of the activated regulator protein to the one or more binding sites for the activated regulator protein. The term "minimal promoter", as used herein, refers to minimal portion of a promoter required to properly initiate transcription. In one embodiment, the second promoter is a minimal promoter comprising, essentially consisting of or consisting of a TATA sequence and/or an mRNA initiation sequence. In one embodiment, the second promoter is a minimal promoter comprising the adenovirus E1b TATA sequence.

In one embodiment, the second expression cassette comprises, essentially consists of or consists of, in 5' to 3' direction, the promoter region, a coding sequence for the molecule of interest and a second polyadenylation signal sequence. The second expression cassette may also comprise one or more synthetic introns, e.g., in the promoter region and/or arranged between the coding sequence for the molecule of interest and the second polyadenylation signal sequence.

According to the present invention, the first polyadenylation signal sequence and the second polyadenylation signal sequence may be the same or different. In one embodiment, the first polyadenylation signal sequence and the second polyadenylation signal sequence are independently selected from the group consisting of a simian virus 40 (SV40) polyadenylation signal sequence, a bovine growth hormone (bGH) polyadenylation signal sequence and a human growth hormone (hGH) polyadenylation signal sequence. In one embodiment, the first polyadenylation signal sequence is a simian virus 40 (SV40) polyadenylation signal sequence, and the second polyadenylation signal sequence is a bovine growth hormone (bGH) polyadenylation signal sequence.

In the context of the present invention, the term "DNA" relates to a molecule, which comprises deoxyribonucleotide residues and preferably is entirely or substantially composed of deoxyribonucleotide residues. "Deoxyribonucleotide" relates to a nucleotide, which lacks a hydroxyl group at the 2'-position of a β-D-ribofuranosyl group. The term "DNA" comprises isolated DNA such as partially or completely purified DNA, essentially pure DNA, synthetic DNA, and recombinantly generated DNA and includes modified DNA, which differs from naturally occurring DNA by addition, deletion, substitution and/or alteration of one or more nucleotides. Such alterations can include addition of non-nucleotide material, such as to the end(s) of a DNA or internally, for example at one or more nucleotides of the DNA. Nucleotides in DNA molecules can also comprise non-standard nucleotides, such as non-naturally occurring nucleotides or chemically synthesized nucleotides. These altered DNAs can be referred to as analogs or analogs of naturally occurring DNA.

The term "molecule of interest", as used herein, refers to a macromolecule, such as but not limited to RNA, a peptide and a polypeptide or protein.

In one embodiment, the molecule of interest is a therapeutically active peptide or protein or a therapeutically active oligo- or polynucleotide. The term "peptide", as used herein, generally relates to substances which include at least 2, at least 3, at least 4, at least 6, at least 8, at least 10, at least 12 or at least 14 and preferably up to 8, 10, 12, 14, 16, 18, 20, 25, 30, 50, or 100 consecutive amino acids which are connected together by peptide bonds. The terms "polypeptide" and "protein", as used herein, relate to large peptides, preferably peptides having more than 100 amino acids, but the terms "peptide", "polypeptide" and "protein" may be used interchangeably herein. The term "oligonucleotide", as used herein, refers to short DNA or RNA molecules, preferably with 30 or less nucleotide residues. The term "polynucleotide", as used herein, refers to long DNA or RNA molecules, preferably with more than 30 nucleotide residues. In one embodiment, the oligo- or polynucleotide is an RNA oligo- or polynucleotide.

In the context of the present invention, the term "RNA" relates to a molecule, which comprises ribonucleotide residues and preferably is entirely or substantially composed of ribonucleotide residues. "Ribonucleotide" relates to a nucleotide with a hydroxyl group at the 2'-position of a β-D-ribofuranosyl group. The RNA may, for example, be a ribozyme, an antisense RNA or an miRNA.

The term "therapeutically active", as used herein, refers to a molecule of interest which has a therapeutic/pharmacologic effect when administered appropriately to a subject suffering from a disease or disorder. Such therapeutic/pharmacologic effect is one that is expected to be related to a beneficial effect on the course or a symptom of the disease or disorder.

In one embodiment, the molecule of interest is a neurotrophic factor. The term "neurotrophic factor", as used herein, refers to proteins that are involved in or responsible for the growth and survival of developing neurons and the maintenance of mature neurons. In one embodiment, the neurotrophic factor is selected from the group consisting of glial cell line-derived neurotrophic factor (GDNF), brain-derived neurotrophic factor (BDNF), neurotrophin 3 (NT-3), nerve growth factor (NGF), neurturin (NRTN), artemin (ARTN) and persephin (PSPN). GDNF, NRTN, ARTN and PSPN are members of the GDNF family of ligands (GFL), which may be preferred neurotrophic factors in accordance with the present invention. In one embodiment, the neurotrophic factor is GDNF.

The molecule of interest may, in accordance with the present invention, also be a peptide or protein or a oligo- or polynucleotide, which is not therapeutically active. Such molecule of interest may, for example, be a fluorescent protein, such as (E)GFP, RFP, YFP and derivatives thereof, or a luminescent protein, such as luciferase and derivatives thereof.

In one embodiment, the AAV vector comprises the nucleotide sequence represented by SEQ ID NO: 1 (or a nucleotide sequence complementary to SEQ ID NO: 1) or a functional variant thereof, wherein the functional variant has a nucleotide sequence which is at least 80% or at least 85% or at least 90% or at least 95% identical to SEQ ID NO: 1 (or to the nucleotide sequence complementary to SEQ ID NO: 1).

In one embodiment, the AAV vector further comprises inverted terminal repeats (ITRs), e.g., AAV-2 ITRs, flanking the first and second expression cassettes (or the nucleotide sequence defined above, if applicable).

The present invention also provides an AAV vector as defined herein, wherein the molecule of interest is a therapeutically active peptide or protein or a therapeutically active oligo- or polynucleotide, for use as a medicament. The term "medicament", as used herein, refers to a substance/composition used in therapy, i.e., in treating, ameliorating or preventing a disease or disorder. According to the invention, the terms "disease" or "disorder" refer to any pathological state. In one embodiment, the disease or disorder is a neurological or neurodegenerative disease.

The present invention also provides an AAV vector as defined herein, wherein the molecule of interest is a neurotrophic factor, for use in treating, ameliorating or preventing a disease or disorder selected from the group consisting of Parkinson's disease, Huntington's disease, spinal cord lesion and an amyloid-related disorder, wherein, preferably, the amyloid-related disorder is selected from the group consisting of Alzheimer's disease (e.g., sporadic Alzheimer's disease or familial Alzheimer's disease), cerebral amyloid angiopathy, dementia, motor neuropathy, Down's syndrome, Creutzfeld Jacob disease, transmissible spongiform encephalopathies, hereditary cerebral hemorrhage with amyloidosis Dutch type, HIV-related dementia, fronto-temporal dementia, Lewy body disease, mixed dementias, head trauma, familial Danish Dementia, familial British Dementia, inclusion body myositis (IBM), neuronal disorder related to aging, and chronic pain.

In one embodiment, the neurotrophic factor is selected from the group consisting of GDNF, BDNF, NT-3, NGF, NRTN, ARTN and PSPN, and the AAV vector is for use in treating, ameliorating or preventing a disease or disorder selected from the group consisting of Parkinson's disease, Huntington's disease and an amyloid-related disorder, wherein, preferably, the amyloid-related disorder is selected from the group consisting of Alzheimer's disease (e.g., sporadic Alzheimer's disease or familial Alzheimer's disease), cerebral amyloid angiopathy, dementia, motor neuropathy, Down's syndrome, Creutzfeld Jacob disease, transmissible spongiform encephalopathies, hereditary cerebral hemorrhage with amyloidosis Dutch type, HIV-related dementia, fronto-temporal dementia, Lewy body disease, mixed dementias, head trauma, familial Danish Dementia, familial British Dementia, inclusion body myositis (IBM), neuronal disorder related to aging, and chronic pain. In one embodiment, the disease or disorder is Parkinson's disease.

In one embodiment, the neurotrophic factor is BDNF, and the AAV vector is for use in treating, ameliorating or preventing a spinal cord lesion.

The present invention further provides the use of the AAV vector as defined herein for the preparation of a medicament for treating, ameliorating or preventing a disease or disorder in a subject, wherein the molecule of interest is a therapeutically active peptide or protein or therapeutically active oligo- or polynucleotide.

The present invention further provides a method for treating, ameliorating or preventing a disease or disorder in a subject, comprising (a) introducing into the subject the AAV vector as defined herein; and (b) administering to the subject the activator molecule to induce expression of the molecule of interest, wherein the molecule of interest is a therapeutically active peptide or protein or therapeutically active oligo- or polynucleotide.

According to the present invention, step (a) may be performed in vivo (by introducing the AAV vector directly into cells of the subject) or at least partially ex vivo (by transferring the AAV vector into isolated cells of the subject or non-autologous cells and introducing the modified cells into the subject or into a different subject). Said introducing may be performed by any suitable method, either systemically (e.g., orally, intravenously, sublingually, transdermally) or locally (e.g., intraperitoneally, intrathecally, intraventricularly or by direct injection into the target tissue or organ). In one embodiment, the AAV vector is introduced into the subject by injection, e.g., by direct injection into the target tissue or organ (e.g., the brain).

The activator molecule may be administered by any suitable method, either systemically (e.g., orally, intravenously, sublingually, transdermally) or locally (e.g., intraperitoneally, intrathecally, intraventricularly or by direct injection into the tissue or organ where the AAV vector was introduced). Administration of the activator molecule can occur once or several times, continuously or intermittently.

The optimal time interval between step (a) and step (b) can be determined for each type of cell/tissue/organ and disease or disorder using only routine techniques.

The term "subject", as used herein, relates to any organism such as a vertebrate, particularly any mammal, including both a human and another mammal, e.g., an animal such as a rodent, a rabbit, a cow, a sheep, a horse, a dog, a cat, a lama, a pig, or a non-human primate (e.g., a monkey). The rodent may be a mouse, rat, hamster, guinea pig, or chinchilla. Preferably, the subject is a human. In one embodiment, a subject is a subject with or suspected of having a disease or disorder, in particular a disease or disorder as disclosed herein, also designated "patient" herein.

In some embodiments of said use or said method, the molecule of interest is a neurotrophic factor and the disease or disorder is selected from the group consisting of Parkinson's disease, Huntington's disease, spinal cord lesion and an amyloid-related disorder, wherein, preferably, the amyloid-related disorder is selected from the group consisting of Alzheimer's disease (e.g., sporadic Alzheimer's disease or familial Alzheimer's disease), cerebral amyloid angiopathy, dementia, motor neuropathy, Down's syndrome, Creutzfeld Jacob disease, transmissible spongiform encephalopathies, hereditary cerebral hemorrhage with amyloidosis Dutch type, HIV-related dementia, fronto-temporal dementia, Lewy body disease, mixed dementias, head trauma, familial Danish Dementia, familial British Dementia, inclusion body myositis (IBM), neuronal disorder related to aging, and chronic pain.

The present invention also provides nucleic acid molecules, in particular DNA molecules, comprised in the AAV vector of the invention. In one embodiment, said nucleic acid molecule is an AAV vector genome comprising the first expression cassette and the second expression cassette as defined herein, wherein the first expression cassette and the second expression cassette are arranged in a tail-to-head configuration. Such nucleic acid molecules are, e.g., provided in the form of an adeno-associated virus (AAV) vector construct, which, preferably, allows the production of the AAV vector of the invention by methods known in the art (e.g., as described in Tereshchenko J. et al., Neurobiol Dis. 2014, 65:35-42; Maddalena A. et al., Mol Ther Nucleic Acids. 2013, 2:e106; and Drinkut A. et al., Mol Ther. 2012, 20:534-543). Such AAV vector construct may, for example, be in the form of a plasmid (referred to as AAV vector plasmid) or in the form of a linear (expression) construct. The term "AAV vector plasmid", as used herein, is meant to refer to a double stranded circular nucleic acid molecule that contains at least a functional portion of an AAV nucleic acid molecule.

The present invention further provides an adeno-associated virus (AAV) vector construct comprising (i) a first expression cassette directing the expression of a regulator protein under the control of a first promoter, wherein the regulator protein is activated in the presence of an activator molecule, and (ii) a second expression cassette comprising a multiple cloning site allowing the insertion of a coding sequence for a molecule of interest, wherein the second expression cassette comprises a promoter region, and the expression of the molecule of interest is induced by binding of the activated regulator protein to the promoter region, wherein the first expression cassette and the second expression cassette are arranged in a tail-to-head configuration.

Such AAV may be referred to as an empty AAV vector construct, i.e., without a coding sequence for a molecule of interest. Preferably, all elements of this empty AAV vector construct are as defined herein in connection with the AAV vector.

In one embodiment, the AAV vector construct comprises the nucleotide sequence represented by SEQ ID NO: 2 (or a nucleotide sequence complementary to SEQ ID NO: 2) or a functional variant thereof, wherein the functional variant has a nucleotide sequence which is at least 80% or at least 85% or at least 90% or at least 95% identical to SEQ ID NO: 2 (or to the nucleotide sequence complementary to SEQ ID NO: 2).

In one embodiment, the AAV vector construct further comprises inverted terminal repeats (ITRs), e.g., AAV-2 ITRs, flanking the first and second expression cassettes (or the nucleotide sequence defined above, if applicable).

In one embodiment, the AAV vector construct comprises a coding sequence for a molecule of interest, which is inserted into said multiple cloning site.

In one embodiment, the AAV vector construct does not comprise a(n) (active) transcriptional silencer, such as a Tet repressor.

Preferably, the AAV vectors of the present invention ensure that, in the absence of the activator molecule, the molecule of interest is not expressed in a host or is expressed in a host at a level which is at most 10-fold or at most 5-fold or at most 4-fold or at most 3-fold or at most 2-fold increased as compared to the normal expression level of the molecule of interest in the host, wherein the host is a cell, tissue or organ.

The terms "part" or "fragment" or "portion" are used interchangeably herein and refer to a continuous element. For example, a part of a structure, such as an amino acid sequence or nucleotide sequence, refers to a continuous element of said structure. For example, a part or fragment of a nucleotide sequence preferably comprises a sequence of at least 6, in particular at least 8, at least 12, at least 15, at least 20, at least 30, at least 50, at least 100, at least 150, at least 160, at least 170, at least 180, at least 190 or at least 200 consecutive nucleotides of the nucleotide sequence.

For the purposes of the present invention, "variants" of an amino acid sequence or nucleotide sequence comprise amino acid/nucleotide insertion variants, amino acid/nucleotide addition variants, amino acid/nucleotide deletion variants and/or amino acid/nucleotide substitution variants. Amino acid/nucleotide insertion variants comprise insertions of single or two or more amino acids/nucleotides in a particular amino acid sequence or nucleotide sequence. In the case of amino acid/nucleotide sequence variants having an insertion, one or more amino acid/nucleotide residues are inserted into a particular site in an amino acid sequence or nucleotide sequence, although random insertion with appropriate screening of the resulting product is also possible. Amino acid/nucleotide addition variants comprise N- and/or C-terminal fusions of one or more amino acids/nucleotides, such as 1, 2, 3, 5, 10, 20, 30, 50, or more amino acids/nucleotides. Amino acid/nucleotide deletion variants are characterized by the removal of one or more amino acids/nucleotides from the sequence, such as by removal of 1, 2, 3, 5, 10, 20, 30, 50, or more amino acids/nucleotide. The deletions may be in any position of the amino acid sequence or nucleotide sequence, for example at the N- and/or C-terminus. Amino acid/nucleotide deletion variants that comprise the deletion at the N-terminal and/or C-terminal end of the amino acid sequence or nucleotide sequence are also called N-terminal and/or C-terminal truncation variants. Amino acid/nucleotide substitution variants are characterized by at least one residue in the sequence being removed and another residue being inserted in its place. In one embodiment, the amino acid/nucleotide substitution variant comprises the substitution of up to 10, 9, 8, 7, 6, 5, 4, 3 or 2 amino acids/nucleotides.

The term "variant", as used herein in connection with a promoter, may also refer to mutants, species variants and homologues of said promoter, including those, which occur naturally.

Alternatively or additionally, a "variant" as used herein, can be characterized by a certain degree of sequence identity to the parent amino acid sequence or nucleotide sequence from which it is derived. More precisely, an amino acid sequence variant in the context of the present invention may exhibit at least 80% sequence identity to its parent amino acid sequence. A nucleotide sequence variant in the context of the present invention may exhibit at least 80% sequence identity to its parent nucleotide sequence. The term "at least 80% identical to", as used herein, refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective parent/reference amino acid sequence or to the respective parent/reference nucleotide sequence. Preferably, the amino acid sequence in question and the parent/reference amino acid sequence exhibit the indicated sequence identity over the entire length of the parent/reference amino acid sequence. Preferably, the nucleotide sequence in question and the parent/reference nucleotide sequence exhibit the indicated sequence identity over the entire length of the parent/reference nucleotide sequence.

The similarity of nucleotide and amino acid sequences, i.e., the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90:5873-5877), with hmmalign (HMMER package, website: hmmer.wus-tl.edu/) or with the CLUSTAL algorithm (Thompson J. D. et al. Nucleic Acids Res. 1994, 22:4673-80) available e.g. at website ebi.ac.uk/Tools/clustalw/; ebi.ac.uk/Tools/clust-alw2/index.html; or npsa-pbil.ibcp.fr/cgi-bin/npsa_automat/.pl?page=/NPSA/npsa_clustalw.html. Preferred parameters used are the default parameters as they are set at website ebi.ac.uk/Tools/clustalw/or ebi.ac.uk/Tools/clustalw2/in-dex.html. The grade of sequence identity (sequence match-ing) may be calculated using e.g. BLAST, BLAT or BlastZ (or BlastX). A similar algorithm is incorporated into the BLASTN and BLASTP programs of Altschul et al. J. Mol. Biol. 1990, 215:403-410. BLAST polynucleotide searches are performed with the BLASTN program, score=100, word length=12, to obtain polynucleotide sequences that are homologous to those nucleic acids which encode F, N, or M2-1. BLAST protein searches are performed with the BLASTP program, score=50, word length=3, to obtain amino acid sequences homologous to the F polypeptide, N polypeptide, or M2-1 polypeptide. To obtain gapped align-ments for comparative purposes, Gapped BLAST is utilized as described in Altschul et al. Nucleic Acids Res. 1997, 25:3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields.

The terms "functional fragment" and "functional variant", as used herein in connection with a promoter, refers to a fragment or variant of a promoter which is functional in the sense that it has the same or essentially the same activity (in particular properly initiating transcription and/or cell-/tis-sue-/organ-specificity, if applicable) as said promoter. The term "functional variant", as used herein in connection with the nucleotide sequence comprised in an AAV vector of the present invention (e.g., the nucleotide sequence of SEQ ID NO: 1 or SEQ ID NO: 2), refers to a variant of said nucleotide sequence which is functional in the sense that it allows the regulatable expression of a molecule of interest to the same or essentially the same degree as the AAV vector comprising said nucleotide sequence (e.g., the nucleotide sequence of SEQ ID NO: 1 or SEQ ID NO: 2), wherein, preferably, in the absence of the activator molecule, the molecule of interest is not expressed in a host or is expressed in a host at a level which is at most 10-fold or at most 5-fold or at most 4-fold or at most 3-fold or at most 2-fold increased as compared to the normal expression level of the molecule of interest in the host, wherein the host is a cell, tissue or organ.

The present invention also provides a host cell comprising the AAV vector of the present invention or a nucleic acid molecule of the present invention, e.g., an AAV vector construct as defined herein. Such host cell may either be a prokaryotic cell (e.g., a bacterial cell) or a eukaryotic cell (e.g., a fungal, plant or animal cell). Preferably, the host cell is an isolated host cell. In one embodiment, the host cell is a producer cell (or producer cell line) allowing the produc-tion of the AAV vector of the present invention, e.g., based on an AAV vector construct as defined herein and with co-transfection of suitable helper constructs, e.g., helper plasmids (see, for example, US 2004/0235174 A1). Suitable producer cells are known to a person skilled in the art and include, for example, HEK293 cells.

The present invention further provides a non-human transgenic animal comprising the AAV vector of the present invention. The term "non-human transgenic animal", as used herein, relates, in particular, to non-human mammals, e.g., a rodent, a rabbit, a cow, a sheep, a horse, a dog, a cat, a lama, a pig, or a non-human primate (e.g., a monkey). The rodent may be a mouse, rat, hamster, guinea pig, or chinchilla.

The present invention further provides a pharmaceutical composition comprising the AAV vector or the host cell of the present invention. A pharmaceutical composition in accordance with the present invention may further comprise one or more carriers and/or excipients, all of which are preferably pharmaceutically acceptable. The term "pharma-ceutically acceptable", as used herein, refers to the non-toxicity of a material, which, preferably, does not interact with the action of the active component of the pharmaceu-tical composition, i.e., the AAV vector or host cell of the present invention. In particular, "pharmaceutically accept-able" means approved by a regulatory agency of the Federal or a state government or listed in the U.S. Pharmacopoeia, European Pharmacopoeia or other generally recognized pharmacopeia for use in animals, and more particularly in humans. The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a subject. Possible carrier substances (e.g., diluents) are, for example, sterile water, Ringer's solution, Lactated Ringer's solution, physiological saline, bacteriostatic saline (e.g., saline containing 0.9% benzyl alcohol), phosphate-buffered saline (PBS), Hank's solution, fixed oils, polyalkylene glycols, hydrogenated naphthalenes and biocompatible lactide polymers, lactide/glycolide copolymers or polyoxyethylene/polyoxy-propyl-ene copolymers. In one embodiment, the carrier is PBS. The resulting solutions or suspensions are preferably isotonic to the blood of the recipient. Suitable carriers and their formu-lations are described in greater detail in Remington's Phar-maceutical Sciences, 17$^{th}$ ed., 1985, Mack Publishing Co. The term "excipient", as used herein, is intended to include all substances which may be present in a pharmaceutical composition and which are not active ingredients, such as salts, binders (e.g., lactose, dextrose, sucrose, trehalose, sorbitol, mannitol), lubricants, thickeners, surface active agents, preservatives, emulsifiers, buffer substances, stabi-lizing agents, flavouring agents or colorants.

The present invention further provides a kit comprising the AAV vector or a nucleic acid molecule, e.g., the AAV vector construct, or the host cell or the pharmaceutical composition of the present invention. As used herein, the term "kit" (also referred to as "kit of parts") refers to an article of manufacture comprising one or more containers and, optionally, a data carrier. Said one or more containers may be filled with one or more of the means or reagents disclosed herein, e.g. one container with an AAV vector of the present invention and one container with the corresponding activator molecule. Additional containers may be included in the kit that contain, e.g., diluents, buffers and further reagents. Said data carrier may be a non-electronical data carrier, e.g., a graphical data carrier such as an information leaflet, an information sheet, a bar code or an access code, or an electronical data carrier such as a floppy disk, a compact disk (CD), a digital versatile disk (DVD), a microchip or another semiconductor-based electronical data carrier. The access code may allow the access to a database, e.g., an internet database, a centralized, or a decentralized database. Said data carrier may comprise instructions for the use of the kit in accordance with the present invention.

The inventor has surprisingly found that the AAV vectors of the present invention allow for the regulatable expression of a molecule of interest, e.g., a therapeutically active peptide or protein or a therapeutically active oligo- or polynucleotide, with very low or even zero expression in the non-induced state ("zero background expression"). Such AAV vectors will allow gene therapeutic approaches that are more safe and have less unwanted side effects than current AAV vector-based approaches.

The present invention is further illustrated by the following examples, which are not to be construed as limiting the scope of the invention.

EXAMPLES

Figure 2:
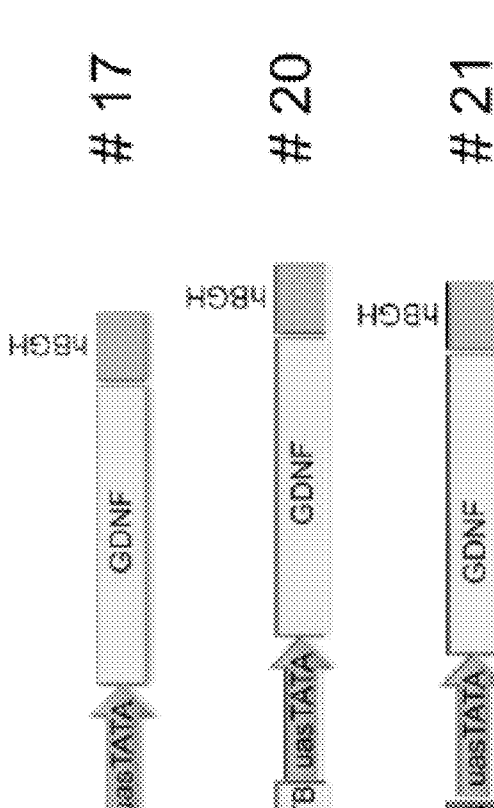
FIG. 2 shows different one-vector GS-GDNF genomes tested by the inventor. SV40=simian virus 40 polyadenylation site; Intron=polynucleotide containing splice donor and acceptor sites; GS=cDNA of the gene switch fusion protein; hSYN1=fragment of human synapsin 1 gene promoter; uasTATA=regulated promoter consisting of six GAL4 binding sites and a minimal TATA promoter plus splice donor and acceptor sites; GDNF=cDNA of GDNF; BGH=bovine growth hormone polyadenylation site; TB=polynucleotide containing synthetic transcription pause and polyadenylation site.
Figure 2:
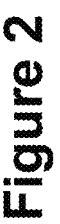

Several different configurations of a one-vector GS-GDNF layout were designed, which were packaged into AAV-5 viral capsids and tested in the rat brain for GDNF production in absence or presence of Mfp. FIG. 2 depicts some of the constructs that were finally assessed, Table 1 shows GDNF levels obtained from rat brains before and after induction with Mfp.

TABLE 1

GFNF levels as determined by ELISA in rat brains, injected with AAV-5 viruses at specified titres. Mfp was given at 3 weeks after vector injection, tissues were prepared at 1 week after Mfp application.

| Vector injected into rat brain | Titre (vg) | GDNF – Mfp (pg/mg tissue) | GDNF + Mfp (pg/mg tissue) |
|---|---|---|---|
| no vector | — | 5 | 5 |
| # 17 | 3 × 10e9 | 650 | 1100 |
| # 20 | 3 × 10e9 | 175 | 900 |

TABLE 1-continued

GFNF levels as determined by ELISA in rat brains, injected with AAV-5 viruses at specified titres. Mfp was given at 3 weeks after vector injection, tissues were prepared at 1 week after Mfp application.

| Vector injected into rat brain | Titre (vg) | GDNF – Mfp (pg/mg tissue) | GDNF + Mfp (pg/mg tissue) |
|---|---|---|---|
| # 21 | 3 × 10e9 | 9 | 1900 |
| # 21 | 1 × 10e9 | 5 | 1300 |

The results shown in Table 1 demonstrate that the layout of vector #17 (see FIG. 2) made it almost useless for regulated gene therapy, as in the non-induced state it produced GDNF levels 130-fold over background, while Mfp induction only increased GDNF levels 2-fold further. Insertion of a small synthetic polynucleotide containing insulator sequences (TB=transcription pause and polyadenylation sites; see vector #20) significantly reduced non-induced GDNF levels and improved the rate of induction, but non-induced GDNF levels were still 35-fold higher than normal rat GDNF brain levels.

Vector #21 contains the same elements as vector #20, except that the expression cassette for GS is inverted, i.e., the two expression cassettes are arranged in a tail-to-head configuration (see FIG. 2 and Table 2). This feature provided dramatically improved performance of the vector, in that non-induced GDNF levels were only 2-fold increased as compared to normal background GDNF levels in the rat brain, while induced GDNF levels were 380-fold over background. Reducing the injected virus titre from 3×10e9 vector genomes to 1×10e9 vector genomes resulted in non-induced GDNF levels indistinguishable from normal rat brain levels, with still 260-fold induction. At four weeks after Mfp induction, GDNF levels in rats injected with AAV-5 #21 at 1×10e9 vg had returned to background levels again. To the inventor's knowledge, this is the first description of any regulated gene transfer system in AAV vectors with zero background expression in the non-induced state, and the first functional one-vector genome layout of the gene switch system in AAV vectors.

The vector genome of the invention (see, for example, SEQ ID NOs: 1 and 2) contains unique restriction sites at strategic positions, allowing easy further manipulation of its layout, for example taking away splice sites for reduced expression levels of the GS fusion protein as well as exchange of promoter elements and/or the transgene/molecule of interest.

TABLE 2

Annotated sequence of an exemplary vector genome
of the present invention (vector #21; SEQ ID NO: 1).

```
        BglII      MluI       BamHI      HindIII         PstI      ApaI
        ------     ------     ------     ------          -------   ------
     1  agatctagga tcacgcgtaa aggatccaaa aaaaagctta aactagactg cagagggccc tgcgtatgag
                                                   >>......'HSYN-Promoter.......>

71  tgcaagtggg ttttaggacc aggatgaggc ggggtggggg tgcctacctg acgaccgacc ccgacccact
        >...............................'HSYN-Promoter..............................>

141  ggacaagcac ccaaccccca ttccccaaat tgcgcatccc ctatcagaga ggggagggg aaacaggatg
        >...............................'HSYN-Promoter..............................>

211  cggcgaggcg cgtgcgcact gccagcttca gcaccgcgga cagtgccttc gcccccgcct ggcggcgcgc
        >...............................'HSYN-Promoter..............................>
```

TABLE 2-continued

Annotated sequence of an exemplary vector genome
of the present invention (vector #21; SEQ ID NO: 1).

```
 281    gccaccgccg cctcagcact gaaggcgcgc tgacgtcact cgccggtccc ccgcaaactc cccttcccgg
        >...............................'HSYN-Promoter..............................>

351    ccaccttggt cgcgtccgcg ccgccgccgg cccagccgga ccgcaccacg cgaggcgcga gatagggggg
        >...............................'HSYN-Promoter..............................>

421    cacgggcgcg accatctgcg ctgcggcgcc ggcgactcag cgctgcctca gtctgcggtg ggcagcggag
        >...............................'HSYN-Promoter..............................>

NheI           AgeI           NcoI
                                       -------        -------        ------
 491    gagtcgtgtc gtgcctgaga gcgcagtcga aagctgctag caaccatcca ccggtcgcca ccatggatag
        >........'HSYN-Promoter.........>>
                                                                    >>.....>

561    ccagcagccc gatctgaaat tgctgtcctc tattgaacag gcttgtgata tttgcaggct taaaaaactc
        >...............................pSwitch...............................>

631    aaatgttcca aagaaaaacc aaagtgtgct aaatgtctga agaacaactg ggaatgccgc tactccccca
        >...............................pSwitch...............................>

701    agaccaagcg ttctccactt actcgcgctc acctgacaga ggtagaaagt aggctggaac gcctagaaca
        >...............................pSwitch...............................>

EcoRV
                                                                    ------
 771    gttgtttttg ttgatattcc caagagaaga cctggacatg attcttaaga tggatagcct gcaagatatc
        >...............................pSwitch...............................>

841    aaggcgctcc tggagtttcc aggcgtcgat cagaaaaagt ttaacaaggt ccgagtcgtc cgagccctag
        >...............................pSwitch...............................>

911    acgccgttgc cctccctcaa cccgtgggcg tgcctaatga aagccaggct ctctcacagc ggtttacttt
        >...............................pSwitch...............................>

981    cagcccaggg caggatatac agcttatacc tcccctgata aatttattga tgagtatcga gccggacgtg
        >...............................pSwitch...............................>

1051    atttacgcag ggcatgataa cactaagcca gacacatctt cttctctcct gaccagccta aaccaactgg
        >...............................pSwitch...............................>

1121    gtgaacggca gcttctgtca gtcgtgaagt ggagcaaatc cctccctgga tttagaaacc tgcacataga
        >...............................pSwitch...............................>

1191    tgaccaaata acacttattc aatactcctg gatgagctta atggtgtttg gtctcggatg gcggtcatat
        >...............................pSwitch...............................>

1261    aagcacgtta gcggccagat gctctacttt gcccctgatt tgattctgaa cgaacaaagg atgaaggaga
        >...............................pSwitch...............................>

1331    gctccttcta tagcctttgt ctgacgatgt ggcaaatccc gcaggagttt gtaaaactgc aagtgagtca
        >...............................pSwitch...............................>

1401    ggaggagttc ctgtgtatga aagttctact gctgctcaat acgatcccct tggaagggct cagatcacag
        >...............................pSwitch...............................>

1471    acgcaattcg aagagatgag gagctcttat attagagagc taattaaggc tattggtctg aggcaaaagg
        >...............................pSwitch...............................>

1541    gtgtcgtgtc cagcagccag agattttacc aacttactaa actactggac aacctacacg acctagtcaa
        >...............................pSwitch...............................>

1611    gcagctccat ctctactgcc tgaacacctt cattcaatcc agagccttat ctgtggaatt tccggaaatg
        >...............................pSwitch...............................>

NcoI
                                       -------
1681    atgagtgagg tcattgcggg gtcaactccc atggaatttc agtatctgcc agacaccgat gacaggcacc
        >...............................pSwitch...............................>

1751    gcatcgaaga gaaacggaaa cggacatacg agaccttcaa gtccattatg aaaaagagtc cctttttctgg
        >...............................pSwitch...............................>
```

TABLE 2-continued

Annotated sequence of an exemplary vector genome
of the present invention (vector #21; SEQ ID NO: 1).

```
1821    ccctaccgac cccagacccc ctccaaggag aatcgcagtg ccttccagga gtagtgcatc agttccgaaa
        >................................pSwitch................................>

NcoI
                                                                                   ------
1891    ccggccccac agccatatcc ttttaccagt tctctgagta ccattaacta cgacgaattt cctaccatgg
        >................................pSwitch................................>

1961    ttttcccctc ggggcaaatt agccaggcgt ccgcgctggc gcccgcgccc cccaggtcc ttccgcaggc
        >................................pSwitch................................>

2031    tccagcccct gctccagccc ccgcaatggt ttctgccctg gcacaagccc ccgcacccgt gcctgtgttg
        >................................pSwitch................................>

2101    gcaccaggcc cgccacaggc cgtggcacct ccggctccta aacctactca ggccggagag ggcacccta
        >................................pSwitch................................>

2171    gtgaggccct gttacagctt caatttgacg acgaggacct cggggctctc cttggcaatt cgacagaccc
        >................................pSwitch................................>

2241    cgctgtgttt acagacctgg cttcggtaga caattctgag tttcagcaac ttctcaacca gggcatcccc
        >................................pSwitch................................>

BstEII
                                                                                   --------
2311    gtagccctc atacaacaga gcccatgtta atggagtacc cagaggctat cacaaggctg gtaaccggcg
        >................................pSwitch................................>

2381    cccaaagacc accagatcct gcaccagcac cactgggagc tcctggttta cccaatggat tattatcagg
        >................................pSwitch................................>

SpeI
                                                                                   ------
2451    agatgaggat ttcagttcca ttgccgatat ggacttcagc gcgcttcttt ctcagatcag ctcttgaact
        >................................pSwitch................................>>

BlnI
              -------
              StuI
              -------
2521    agtaaaaggc ctaggtaagt atcaaggtta caagacaggt ttaaggagac cacatagaaa ctgggcttgt
              >>................................'INTRON................................>
                    >>

2591    cgagacagag aagactcttg cgtttctgat aggcacctat tggtcttact gacatccact ttgcctttct
        >................................'INTRON................................>
                    >>

StuI                              PsiI
              ------                            ------
2661    ctccacaggt gtaggccttt cgagcaactt gtttattgca gcttataatg gttacaaata aagcaatagc
        >.'INTRON.>>
              >>...>>
                    >>........................SV40-pA........................>

2731    atcacaaatt tcacaaataa agcatttttt tcactgcatt ctagttgtgg tttgtccaaa ctcatcaatg
        >................................SV40-pA................................>
                                                            >>

XbaI
                                          ------
2801    tatcttatca tgtctggatc gtctagcatc gaagatccac tagatgcata aatctagaca ataaaatatc
        >..............SV40-pA..............>>
                                                      >>...TB'...>

ClaI
                                    -------
2871    tttatttca ttacatctgt gtgttggttt tttgtgtgaa tcgatagtac taacatacgc tctccatcaa
        >....................TB'....................>>
                                          >>.............'TB..............>

2941    aacaaaacga aacaaaacaa actagcaaaa taggctgtcc ccagtgcaag tgcaggtgcc agaacatttc
        >................................'TB................................>

ApaI
              -------
```

TABLE 2-continued

Annotated sequence of an exemplary vector genome
of the present invention (vector #21; SEQ ID NO: 1).

```
3011   tctattaggg cccaagcgga gtactgtcct ccgagtggag tactgtcctc cgagcggagt actgtcctcc
       >>>
                    >>.....GAL4......>>
                                         >>.....GAL4 .....>>
                                                              >>.....GAL4.....>

3081   gagtcgaggg tcgaagcgga gtactgtcct ccgagtggag tactgtcctc cgagcggagt actgtcctcc
       >
                    >>.....GAL4 .....>>
                                         >>.....GAL4 .....>>
                                                              >>.....GAL4.....>

EcoRV
                                    ------
                              XhoI
                              -------
3151   gagtcgacta gagggtatat aatggatctc gagatatcgg agctcgttta gtgaaccgtc agatcgcctg
       >
                    >>...TATA....>>
                                                    >>...........................>
                                                      > +1 of 1.9IE transcript 3221   gagacgccat ccacgctgtt ttgacctcca tagaagacac cgggaccgat ccagcctccg cggccgggaa
       >....................HCMV IE 3 from TATA (mRNA 5end).....................>

PacI
                                    ---------
3291   cggtgcattg aacgcgcat tccccgtgtt aattaacagg taagtgtctt cctcctgttt ccttcccctg
       >...........................>>
                                         >>.............IVS8'.............>

PstI                      NheI
                              -------                   -------
3361   ctattctgct caaccttcct atcagaaact gcagtatctg tatttttgct agcagtaata ctaacggttc
       >...................................IVS8'...................................>

KpnI
                        -------
                  MfeI              AgeI          NcoI
                  ------            -------        -------
3431   ttttttctc ttcacaggcc accaattggt accgagctac cggtcgccac catgggaaag ttatgggatg
       >......IVS8'.....>>
                                                    >>......GDNF.......>

3501   tcgtggctgt ctgcctggtg ttgctccaca ccgcgtctgc cttcccgctg cccgccggta agaggcttct
       >...................................GDNF...................................>

3571   cgaagcgccc gccgaagacc actccctcgg ccaccgccgc gtgcccttcg cgctgaccag tgactccaat
       >...................................GDNF...................................>

3641   atgcccgaag attatcctga ccagtttgat gacgtcatgg attttattca agccaccatc aaaagactga
       >...................................GDNF...................................>

BstEII                                        PstI
          -------                                       -------
3711   aaaggtcacc agataaacaa gcggcggcac ttcctcgaag agagaggaac cggcaagctg cagctgccag
       >...................................GDNF...................................>

3781   cccagagaac agcagaggga aaggtcgcag aggccagagg ggcaaaaatc gggggtgcgt cttaactgca
       >...................................GDNF...................................>

3851   atacacttaa atgtcactga cttgggtttg ggctacgaaa ccaaggagga actgatcttt cgatattgta
       >...................................GDNF...................................>

3921   gcggttcctg tgaagcggcc gagacaatgt acgacaaaat actaaaaaat ctgtctcgaa gtagaaggct
       >...................................GDNF...................................>

3991   aacaagtgac aaggtaggcc aggcatgttg caggccggtc gccttcgacg acgacctgtc gttttttagac
       >...................................GDNF...................................>

NotI
                                                                      --------
4061   gacagcctgg tttaccatat cctaagaaag cattccgcta aacggtgtgg atgtatctga gcggccgcac
       >...............................GDNF...............................>>

BclI
                  -------
```

TABLE 2-continued

Annotated sequence of an exemplary vector genome
of the present invention (vector #21; SEQ ID NO: 1).

```
4131    cgtcgactag agctcgctga tcagcctcga ctgtgccttc tagttgccag ccatctgttg tttgcccctc
                >>.........................bGH pA..........................>

4201    ccccgtgcct tccttgaccc tggaaggtgc cactcccact gtcctttcct aataaaatga ggaaattgca
                >.................................bGH pA.................................>

4271    tcgcattgtc tgagtaggtg tcattctatt ctggggggtg gggtggggca ggacagcaag ggggaggatt
                >.................................bGH pA.................................>

SphI           BglII
                        -------        ------
4341    gggaagacaa tagcagggca tgctgggggag agatct
                >....bGH pA....>>
```

In the recombinant virus, i.e., in the complete AAV vector, this sequence was flanked by the AAV-2 inverted terminal repeats.

The invention claimed is:

1. An adeno-associated virus (AAV) vector comprising (i) a first expression cassette comprising a first promoter and a coding sequence for a regulator protein, wherein the first promoter directs expression of the regulator protein, wherein the regulator protein is activated in the presence of an activator molecule, and wherein the regulator protein comprises a GAL4 DNA binding domain, a progesterone receptor ligand binding domain, and the p65 transactivation domain from NF-kappaB, and (ii) a second expression cassette directing the expression of comprising a promoter region and a coding sequence for a molecule of interest, wherein the promoter region regulates expression of the molecule of interest, wherein the promoter region comprises one or more GAL4 binding sites and a second promoter, and wherein, and the expression of the molecule of interest is induced by binding of the activated regulator protein to the promoter region, wherein the first expression cassette and the second expression cassette are arranged in a tail-to-head configuration, and wherein the first expression cassette and the second expression cassette are separated by a transcription blocker sequence comprising a transcription pause site and a polyadenylation signal sequence.

2. The AAV vector of claim 1, wherein the first promoter has one or more of the following features:

(i) it is a constitutive promoter;

(ii) it is selected from the group consisting of cell-specific promoters, tissue-specific promoters and organ-specific promoters; (iii) it is selected from the group consisting of human synapsin 1 gene (hSYN1) promoter, tubulin alpha 1 (Tal) promoter, glial fibrillary acidic protein (GFAP) promoter, cytomegalovirus (CMV) promoter, and human beta-actin-CMV hybrid promoter.

3. The AAV vector of claim 1, wherein the activator molecule is mifepristone (Mfp).

4. The AAV vector of claim 1, wherein the first expression cassette comprises, in 5' to 3' direction, the first promoter, a coding sequence for the regulator protein and a first polyadenylation signal sequence.

5. The AAV vector of claim 4, wherein the first expression cassette further comprises a synthetic intron arranged between the coding sequence for the regulator protein and the first polyadenylation signal sequence.

6. The AAV vector of claim 1, wherein the promoter region further comprises a synthetic intron.

7. The AAV vector of claim 1, wherein the second promoter is a minimal promoter which is induced by the binding of the activated regulator protein to the one or more GAL4 binding sites.

8. The AAV vector of claim 7, wherein the second promoter is a minimal promoter comprising a TATA sequence and/or an mRNA initiation sequence.

9. The AAV vector of claim 1, wherein the molecule of interest is a therapeutically active peptide or protein or a therapeutically active oligo- or polynucleotide.

10. The AAV vector of claim 9, wherein the molecule of interest is a neurotrophic factor.

11. The AAV vector of claim 10, wherein the neurotrophic factor is glial cell line-derived neurotrophic factor (GDNF).

12. The AAV vector construct of claim 9, wherein the AAV vector construct comprises the nucleotide sequence of SEQ ID NO: 2.

13. The AAV vector of claim 1, comprising, in 5' to 3' direction, the first promoter, the coding sequence for the regulator protein, an intron, a first polyadenylation signal sequence, the transcription blocker sequence, the promoter region, the coding sequence for the molecule of interest and a second polyadenylation signal sequence.

14. The AAV vector of claim 13, wherein the first polyadenylation signal sequence is a simian virus 40 (SV40) polyadenylation signal sequence, and wherein the second polyadenylation signal sequence is a bovine growth hormone (bGH) polyadenylation signal sequence.

15. The AAV vector of claim 13, wherein the promoter region comprises six GAL4 binding sites.

16. The AAV vector of claim 13, wherein the regulator protein is encoded by the polynucleotide sequence set forth in the 560-2515 segment of the nucleotide sequence of SEQ ID NO:1.

17. The AAV vector of claim 1, wherein the AAV vector comprises the nucleotide sequence of SEQ ID NO: 1.

18. The AAV vector of claim 1, wherein the first promoter is a promoter.

19. An AAV vector construct comprising (i) a first expression cassette comprising a first promoter and a coding sequence for a regulator protein, wherein the first promoter directs expression of the regulator protein under the control of a first promoter, wherein the regulator protein is activated in the presence of an activator molecule, and wherein the regulator protein comprises a GAL4 DNA binding domain, a progesterone receptor ligand binding domain, and the p65 transactivation domain from NF-kappaB, and (ii) a second expression cassette comprising a promoter region and a multiple cloning site allowing the insertion of a coding sequence for a molecule of interest, wherein the promoter region regulates expression of the molecule of interest following insertion of the coding sequence for the molecule of interest, wherein the promoter region comprises one or more GAL4 binding sites and a second promoter, and wherein the expression of the molecule of interest is induced by binding of the activated regulator protein to the promoter region, wherein the first expression cassette and the second expression cassette are arranged in a tail-to-head configuration, and wherein the first expression cassette and the second expression cassette are separated by a transcription blocker sequence comprising a transcription pause site and a polyadenylation signal sequence.

* * * * *

SEQUENCE LISTING

<160> NUMBER OF SEQ ID NOS: 2

<210> SEQ ID NO 1
<211> LENGTH: 4376
<212> TYPE: DNA
<213> ORGANISM: Artificial Sequence
<220> FEATURE:
<223> OTHER INFORMATION: Vector #21

<400> SEQUENCE: 1

```
agatctagga tcacgcgtaa aggatccaaa aaaaagctta aactagactg cagagggccc        60
tgcgtatgag tgcaagtggg ttttaggacc aggatgaggc ggggtggggg tgcctacctg       120
acgaccgacc ccgacccact ggacaagcac ccaacccccca ttccccaaat tgcgcatccc      180
ctatcagaga gggggagggg aaacaggatg cggcgaggcg cgtgcgcact gccagcttca       240
gcaccgcgga cagtgccttc gcccccgcct ggcggcgcgc gccaccgccg cctcagcact       300
gaaggcgcgc tgacgtcact cgccggtccc ccgcaaactc ccttccggg  ccaccttggt       360 cgcgtccgcg ccgccgccgg cccagccgga ccgcaccacg cgaggcgcga gatagggggg      420
cacgggcgcg accatctgcg ctgcggcgcc ggcgactcag cgctgcctca gtctgcggtg       480
ggcagcggag gagtcgtgtc gtgcctgaga gcgcagtcga aagctgctag caaccatcca       540
ccggtcgcca ccatggatag ccagcagccc gatctgaaat tgctgtcctc tattgaacag       600
gcttgtgata tttgcaggct taaaaaactc aaatgttcca aagaaaaacc aaagtgtgct       660
aaatgtctga agaacaactg ggaatgccgc tactcccccca agaccaagcg ttctccactt       720
actcgcgctc acctgacaga ggtagaaagt aggctggaac gcctagaaca gttgtttttg       780
ttgatattcc caagagaaga cctggacatg attcttaaga tggatagcct gcaagatatc       840
aaggcgctcc tggagtttcc aggcgtcgat cagaaaaagt ttaacaaggt ccgagtcgtc       900
cgagccctag acgccgttgc cctccctcaa cccgtgggcg tgcctaatga aagccaggct       960
ctctcacagc ggtttacttt cagcccaggg caggatatac agcttatacc tcccctgata      1020
aatttattga tgagtatcga gccggacgtg atttacgcag ggcatgataa cactaagcca      1080
gacacatctt cttctctcct gaccagccta aaccaactgg gtgaacggca gcttctgtca      1140
gtcgtgaagt ggagcaaatc cctccctgga tttagaaacc tgcacataga tgaccaaata      1200
acacttattc aatactcctg gatgagctta atggtgtttg gtctcggatg gcggtcatat      1260
aagcacgtta gcggccagat gctctacttt gcccctgatt tgattctgaa cgaacaaagg      1320
```

-continued

```
atgaaggaga gctccttcta tagcctttgt ctgacgatgt ggcaaatccc gcaggagttt    1380
gtaaaactgc aagtgagtca ggaggagttc ctgtgtatga aagttctact gctgctcaat    1440
acgatcccct tggaagggct cagatcacag acgcaattcg aagagatgag gagctcttat    1500
attagagagc taattaaggc tattggtctg aggcaaaagg gtgtcgtgtc cagcagccag    1560
agattttacc aacttactaa actactggac aacctacacg acctagtcaa gcagctccat    1620
ctctactgcc tgaacacctt cattcaatcc agagccttat ctgtggaatt ccggaaatg     1680 atgagtgagg tcattgcggg gtcaactccc atggaatttc agtatctgcc agacaccgat    1740
gacaggcacc gcatcgaaga gaaacggaaa cggacatacg agaccttcaa gtccattatg    1800
aaaaagagtc cctttctgg ccctaccgac cccagacccc ctccaaggag aatcgcagtg      1860
ccttccagga gtagtgcatc agttccgaaa ccggccccac agccatatcc ttttaccagt     1920
tctctgagta ccattaacta cgacgaattt cctaccatgg tttttcccctc ggggcaaatt    1980 agccaggcgt ccgcgctggc gcccgcgccc ccccaggtcc ttccgcaggc tccagcccct     2040
gctccagccc ccgcaatggt ttctgccctg gcacaagccc ccgcacccgt gcctgtgttg     2100
gcaccaggcc cgccacaggc cgtggcacct ccggctccta aacctactca ggccggagag     2160 ggcacccta gtgaggccct gttacagctt caatttgacg acgaggacct cggggctctc      2220
cttggcaatt cgacagaccc cgctgtgttt acagacctgg cttcggtaga caattctgag     2280
tttcagcaac ttctcaacca gggcatcccc gtagcccctc atacaacaga gcccatgtta     2340
atggagtacc cagaggctat cacaaggctg gtaaccggcg cccaaagacc accagatcct     2400
gcaccagcac cactgggagc tcctggttta cccaatggat tattatcagg agatgaggat     2460
ttcagttcca ttgccgatat ggacttcagc gcgcttcttt ctcagatcag ctcttgaact     2520
agtaaaaggc ctaggtaagt atcaaggtta caagacaggt ttaaggagac cacatagaaa     2580
ctgggcttgt cgagacagag aagactcttg cgtttctgat aggcacctat tggtcttact     2640
gacatccact ttgcctttct ctccacaggt gtaggccttt cgagcaactt gtttattgca     2700
gcttataatg gttacaaata aagcaatagc atcacaaatt tcacaaataa agcattttt      2760 tcactgcatt ctagttgtgg tttgtccaaa ctcatcaatg tatcttatca tgtctggatc     2820
gtctagcatc gaagatccac tagatgcata aatctagaca ataaaatatc tttattttca    2880
ttacatctgt gtgttggttt tttgtgtgaa tcgatagtac taacatacgc tctccatcaa     2940
aacaaaacga aacaaaacaa actagcaaaa taggctgtcc ccagtgcaag tgcaggtgcc     3000
agaacatttc tctattaggg cccaagcgga gtactgtcct ccgagtggag tactgtcctc     3060
cgagcggagt actgtcctcc gagtcgaggg tcgaagcgga gtactgtcct ccgagtggag     3120
tactgtcctc cgagcggagt actgtcctcc gagtcgacta gagggtatat aatggatctc     3180
gagatatcgg agctcgttta gtgaaccgtc agatcgcctg gagacgccat ccacgctgtt     3240
ttgacctcca tagaagacac cgggaccgat ccagcctccg cggccgggaa cggtgcattg     3300
gaacgcgcat tccccgtgtt aattaacagg taagtgtctt cctcctgttt ccttcccctg     3360
ctattctgct caaccttcct atcagaaact gcagtatctg tattttttgct agcagtaata    3420 ctaacggttc ttttttctc ttcacaggcc accaattggt accgagctac cggtcgccac      3480
catgggaaag ttatgggatg tcgtggctgt ctgcctggtg ttgctccaca ccgcgtctgc     3540
cttcccgctg cccgccggta agaggcttct cgaagcgccc gccgaagacc actccctcgg     3600
ccaccgccgc gtgcccttcg cgctgaccag tgactccaat atgcccgaag attatcctga    3660
ccagtttgat gacgtcatgg attttattca agccaccatc aaaagactga aaaggtcacc    3720
```

-continued

```
agataaacaa gcggcggcac ttcctcgaag agagaggaac cggcaagctg cagctgccag    3780
cccagagaac agcagaggga aaggtcgcag aggccgagg ggcaaaaatc gggggtgcgt    3840
cttaactgca atacacttaa atgtcactga cttgggtttg ggctacgaaa ccaaggagga    3900
actgatcttt cgatattgta gcggttcctg tgaagcggcc gagacaatgt acgacaaaat    3960
actaaaaaat ctgtctcgaa gtagaaggct aacaagtgac aaggtaggcc aggcatgttg    4020
caggccggtc gccttcgacg acgacctgtc gttttagac gacagcctgg tttaccatat    4080
cctaagaaag cattccgcta aacggtgtgg atgtatctga gcggccgcac cgtcgactag    4140
agctcgctga tcagcctcga ctgtgccttc tagttgccag ccatctgttg tttgcccctc    4200
ccccgtgcct tccttgaccc tggaaggtgc cactcccact gtcctttcct aataaaatga    4260
ggaaattgca tcgcattgtc tgagtaggtg tcattctatt ctggggggtg gggtggggca    4320
ggacagcaag ggggaggatt gggaagacaa tagcagggca tgctggggag agatct    4376
```

<210> SEQ ID NO 2
<211> LENGTH: 3737
<212> TYPE: DNA
<213> ORGANISM: Artificial Sequence
<220> FEATURE:
<223> OTHER INFORMATION: Empty vector #21

<400> SEQUENCE: 2

```
agatctagga tcacgcgtaa aggatccaaa aaaaagctta aactagactg cagagggccc      60
tgcgtatgag tgcaagtggg ttttaggacc aggatgaggc ggggtggggg tgcctacctg     120
acgaccgacc ccgacccact ggacaagcac ccaaccccca ttccccaaat tgcgcatccc     180
ctatcagaga ggggagggg aaacaggatg cggcgaggcg cgtgcgcact gccagcttca     240
gcaccgcgga cagtgccttc gccccgcct ggcggcgcgc gccaccgccg cctcagcact     300
gaaggcgcgc tgacgtcact cgccggtccc ccgcaaactc cccttcccgg ccaccttggt     360
cgcgtccgcg ccgccgccgg cccagccgga ccgcaccacg cgaggcgcga gatagggggg     420
cacgggcgcg accatctgcg ctgcggcgcc ggcgactcag cgctgcctca gtctgcggtg     480
ggcagcggag gagtcgtgtc gtgcctgaga gcgcagtcga aagctgctag caaccatcca     540
ccggtcgcca ccatggatag ccagcagccc gatctgaaat tgctgtcctc tattgaacag     600
gcttgtgata tttgcaggct taaaaaactc aaatgttcca agaaaaaacc aaagtgtgct     660
aaatgtctga agaacaactg ggaatgccgc tactccccca agaccaagcg ttctccactt     720
actcgcgctc acctgacaga ggtagaaagt aggctggaac gcctagaaca gttgtttttg     780
ttgatattcc aagagaaga cctggacatg attcttaaga tggatagcct gcaagatatc     840
aaggcgctcc tggagtttcc aggcgtcgat cagaaaaagt ttaacaaggt ccgagtcgtc     900
cgagccctag acgccgttgc cctccctcaa cccgtgggcg tgcctaatga aagccaggct     960
ctctcacagc ggtttacttt cagcccaggg caggatatac agcttatacc tcccctgata    1020
aatttattga tgagtatcga gccggacgtg atttacgcag ggcatgataa cactaagcca    1080
gacacatctt cttctctcct gaccagccta aaccaactgg gtgaacggca gcttctgtca    1140
gtcgtgaagt ggagcaaatc cctccctgga tttagaaacc tgcacataga tgaccaaata    1200
acacttattc aatactcctg gatgagctta atggtgtttg gtctcggatg gcggtcatat    1260
aagcacgtta gcggccagat gctctacttt gcccctgatt tgattctgaa cgaacaaagg    1320
atgaaggaga gctccttcta tagcctttgt ctgacgatgt ggcaaatccc gcaggagttt    1380
```

-continued

```
gtaaaactgc aagtgagtca ggaggagttc ctgtgtatga aagttctact gctgctcaat   1440
acgatcccct tggaagggct cagatcacag acgcaattcg aagagatgag gagctcttat   1500
attagagagc taattaaggc tattggtctg aggcaaaagg gtgtcgtgtc cagcagccag   1560
agattttacc aacttactaa actactggac aacctacacg acctagtcaa gcagctccat   1620
ctctactgcc tgaacacctt cattcaatcc agagccttat ctgtggaatt ccggaaatg   1680 atgagtgagg tcattgcggg gtcaactccc atggaatttc agtatctgcc agacaccgat   1740
gacaggcacc gcatcgaaga gaaacggaaa cggacatacg agaccttcaa gtccattatg   1800
aaaaagagtc ccttttctgg ccctaccgac cccagacccc ctccaaggag aatcgcagtg   1860
ccttccagga gtagtgcatc agttccgaaa ccggccccac agccatatcc ttttaccagt   1920
tctctgagta ccattaacta cgacgaattt cctaccatgg ttttcccctc ggggcaaatt   1980
agccaggcgt ccgcgctggc gcccgcgccc ccccaggtcc ttccgcaggc tccagcccct   2040
gctccagccc ccgcaatggt ttctgccctg gcacaagccc ccgcacccgt gcctgtgttg   2100
gcaccaggcc cgccacaggc cgtggcacct ccggctccta aacctactca ggccggagag   2160
ggcaccctta gtgaggccct gttacagctt caatttgacg acgaggacct cggggctctc   2220
cttggcaatt cgacagaccc cgctgtgttt acagacctgg cttcggtaga caattctgag   2280
tttcagcaac ttctcaacca gggcatcccc gtagcccctc atacaacaga gcccatgtta   2340
atggagtacc cagaggctat cacaaggctg gtaaccggcg cccaaagacc accagatcct   2400
gcaccagcac cactgggagc tcctggttta cccaatggat tattatcagg agatgaggat   2460
ttcagttcca ttgccgatat ggacttcagc gcgcttcttt ctcagatcag ctcttgaact   2520
agtaaaaggc ctaggtaagt atcaaggtta caagacaggt ttaaggagac cacatagaaa   2580
ctgggcttgt cgagacagag aagactcttg cgtttctgat aggcacctat tggtcttact   2640
gacatccact ttgcctttct ctccacaggt gtaggccttt cgagcaactt gtttattgca   2700
gcttataatg gttacaaata aagcaatagc atcacaaatt tcacaaataa agcattttt   2760 tcactgcatt ctagttgtgg tttgtccaaa ctcatcaatg tatcttatca tgtctggatc   2820
gtctagcatc gaagatccac tagatgcata aatctagaca ataaaatatc tttattttca   2880
ttacatctgt gtgttggttt tttgtgtgaa tcgatagtac taacatacgc tctccatcaa   2940
aacaaaacga aacaaaacaa actagcaaaa taggctgtcc ccagtgcaag tgcaggtgcc   3000
agaacatttc tctattaggg cccaagcgga gtactgtcct ccgagtggag tactgtcctc   3060
cgagcggagt actgtcctcc gagtcgaggg tcgaagcgga gtactgtcct ccgagtggag   3120
tactgtcctc cgagcggagt actgtcctcc gagtcgacta gagggtatat aatggatctc   3180
gagatatcgg agctcgttta gtgaaccgtc agatcgcctg gagacgccat ccacgctgtt   3240
ttgacctcca tagaagacac cgggaccgat ccagcctccg cggccgggaa cggtgcattg   3300
gaacgcgcat tccccgtgtt aattaacagg taagtgtctt cctcctgttt ccttccctg   3360 ctattctgct caaccttcct atcagaaact gcagtatctg tatttttgct agcagtaata   3420
ctaacggttc ttttttttctc ttcacaggcc accaattggt accgagctac cggtcgccac   3480
cgcggccgca ccgtcgacta gagctcgctg atcagcctcg actgtgcctt ctagttgcca   3540
gccatctgtt gtttgcccct ccccccgtgcc ttccttgacc ctggaaggtg ccactcccac   3600
tgtcctttcc taataaaatg aggaaattgc atcgcattgt ctgagtaggt gtcattctat   3660
```

-continued

```
tctgggggt ggggtggggc aggacagcaa gggggaggat tgggaagaca atagcagggc    3720 atgctggggga gagatct                                                 3737
```